United States Patent
Lutze et al.

(10) Patent No.: US 12,312,313 B2
(45) Date of Patent: May 27, 2025

(54) ENERGY-EFFICIENT PROCESS FOR REMOVING BUTENES FROM C4-HYDROCARBON STREAMS

(71) Applicant: Evonik Oxeno GmbH & Co. KG, Marl (DE)

(72) Inventors: Philip Lutze, Dinslaken (DE); Stephan Peitz, Oer-Erkenschwick (DE); Armin Matthias Rix, Marl (DE); Tanita Valèrie Six, Dortmund (DE); Moritz Schröder, Muenster (DE); Niklas Paul, Marl (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 161 days.

(21) Appl. No.: 18/260,069

(22) PCT Filed: Jan. 21, 2022

(86) PCT No.: PCT/EP2022/051366
§ 371 (c)(1),
(2) Date: Jun. 30, 2023

(87) PCT Pub. No.: WO2022/161869
PCT Pub. Date: Aug. 4, 2022

(65) Prior Publication Data
US 2024/0059633 A1  Feb. 22, 2024

(30) Foreign Application Priority Data
Jan. 27, 2021 (EP) ..................................... 21153661

(51) Int. Cl.
*C07C 7/11*    (2006.01)
*C07C 7/04*    (2006.01)

(52) U.S. Cl.
CPC . *C07C 7/11* (2013.01); *C07C 7/04* (2013.01)

(58) Field of Classification Search
CPC .... C07C 7/11; C07C 7/04; C07C 7/08; C07C 11/08; B01D 3/007; B01D 3/143; B01D 3/40; B01D 5/006; B01D 5/0075
See application file for complete search history.

(56) References Cited

U.S. PATENT DOCUMENTS

| 11,629,109 B2 | 4/2023 | Lutze et al. | |
| 2005/0154246 A1* | 7/2005 | Adrian | C07C 7/08 585/862 |
| 2014/0124358 A1* | 5/2014 | Schwint | C07C 7/08 202/168 |

(Continued)

OTHER PUBLICATIONS

U.S. Office Action dated Dec. 7, 2023, in U.S. Appl. No. 18/260,114, 14 pages.

(Continued)

*Primary Examiner* — Ali Z Fadhel
(74) *Attorney, Agent, or Firm* — Grüneberg and Myers PLLC

(57) ABSTRACT

A process for removing butenes from C4-hydrocarbon streams containing butanes and butenes involves extractive distillation with a suitable solvent. The process also involves heat integration, which allows utilization of the heat of the solvent for heating and/or at least partly evaporating various streams.

19 Claims, 5 Drawing Sheets

(56) References Cited

U.S. PATENT DOCUMENTS

2022/0411352 A1    12/2022    Lutze et al.

OTHER PUBLICATIONS

U.S. Office Action dated Oct. 5, 2023, in U.S. Appl. No. 18/260,099, 7 pages.
International Search Report dated Apr. 22, 2022, in PCT/EP2022/051366, with English translation, 5 pages.
Written Opinion dated Apr. 22, 2022, in PCT/EP2022/051366, with English translation, 8 pages.
European Search Report dated Jul. 26, 2021, in European Application No. 21153661.0, 6 pages.
U.S. Appl. No. 18/260,114, filed Jun. 30, 2023, Lutze et al.
U.S. Appl. No. 18/260,071, filed Jun. 30, 2023, Lutze et al.
U.S. Appl. No. 18/260,099, filed Jun. 30, 2023, Lutze et al.
U.S. Appl. No. 18/260,102, filed Jun. 30, 2023, Six et al.

\* cited by examiner

ENERGY-EFFICIENT PROCESS FOR REMOVING BUTENES FROM C4-HYDROCARBON STREAMS

CROSS-REFERENCE TO RELATED APPLICATIONS

This application is the National Stage entry under § 371 of International Application No. PCT/EP2022/051366, filed on Jan. 21, 2022, and which claims the benefit of priority to European Application No. 21153661.0, filed on Jan. 27, 2021. The content of each of these applications is hereby incorporated by reference in its entirety.

BACKGROUND OF THE INVENTION

Field of the Invention

The present invention relates to a process for separation of butenes from C4-hydrocarbon streams containing not only the butenes but also butanes by extractive distillation with a suitable solvent. The process according to the invention features heat integration with which the heat of the solvent is utilized for heating and/or at least partially evaporating different streams.

Description of Related Art

The separation of butane-butene mixtures by extractive distillation is known per se. This employs an aprotic solvent (for example N-methyl-2-pyrrolidone (NMP) or acetonitrile (ACN)) to increase the relative volatility of the alkanes compared to the alkenes. In one extractive distillation column, the absorber, the butenes are preferably dissolved in the solvent and the butanes are separated as tops product. The laden solvent is subsequently freed of the butenes in a stripping column, the desorber, at elevated temperature and/or reduced pressure, and said butenes are obtained in enriched form as tops product. The solvent freed of butenes is then recycled to the extractive distillation.

Heat integration is of great importance to the economy of the process due to the high solvent to feed ratio. Hot solvent is obtained at the bottom of the desorber and the energy content thereof may be utilized in various ways. US 2014/0124358 A1 presents a process for selective extraction of olefins which is said to solve the problem of heat integration. This document proposes utilizing the energy content of the hot solvent for heating a sidestream from the desorber, for heating the bottoms product of the absorber which is passed to the desorber, for heating one or more sidestreams of the absorber and for preheating the feed stream.

However, the solution proposed in the prior art can solve the problem of ideally full recovery of the energy streams present in the system only incompletely or via relatively complex constructions.

SUMMARY OF THE INVENTION

It is accordingly the object of the present invention to provide a process where an improved, ideally maximum possible, energy recovery is achieved and this is done in a way with less plant engineering complexity.

This object is achievable by the embodiment of the process described below. Preferred embodiments are also specified below. The process according to the invention is a process for separating butenes from a C4-hydrocarbon stream which contains at least butenes and butanes by extractive distillation with a solvent, wherein the process comprises the steps of:

a. at least partially evaporating the liquid C4-hydrocarbon stream in a feed evaporator, supplying the gaseous C4-hydrocarbon stream and supplying the liquid solvent, preferably NMP, above the C4-hydrocarbon stream to an absorber in which the C4-hydrocarbon stream and the solvent are contacted with one another to transfer predominantly butenes from the C4-hydrocarbon stream to the solvent, wherein the thus-laden solvent, preferably NMP, is collected in a liquid collector of the absorber, passed through an absorber evaporator and then passed into the bottom of the absorber below the liquid collector to outgas predominantly butanes from the laden solvent, preferably NMP, and wherein the laden solvent, preferably NMP, is subsequently passed to a desorber as bottoms stream;

b. supplying the laden solvent, preferably NMP, to the desorber, the bottom of which is at an elevated temperature and preferably a lower pressure relative to the bottom of the absorber and in which the butenes are separated from the solvent, preferably NMP, to obtain at the top of the desorber a stream enriched in butenes, wherein a solvent, preferably NMP, at least partially freed of butenes is collected in a liquid collector of the desorber, passed through a desorber evaporator and then passed into the bottom of the desorber below the liquid collector to outgas any butenes remaining in the solvent and wherein the solvent, preferably NMP, is subsequently recycled to the absorber as bottoms stream;

wherein the heat of the solvent withdrawn as a bottoms stream of the desorber, preferably of the NMP, is used at least partially for heat integration by employing the heat of the solvent, preferably of the NMP, in at least one respective heat exchanger for preheating the laden solvent passed to the desorber, preferably NMP, for evaporation in the absorber evaporator and for evaporation of the liquid C4-hydrocarbon stream.

DETAILED DESCRIPTION OF THE INVENTION

Figure 1:
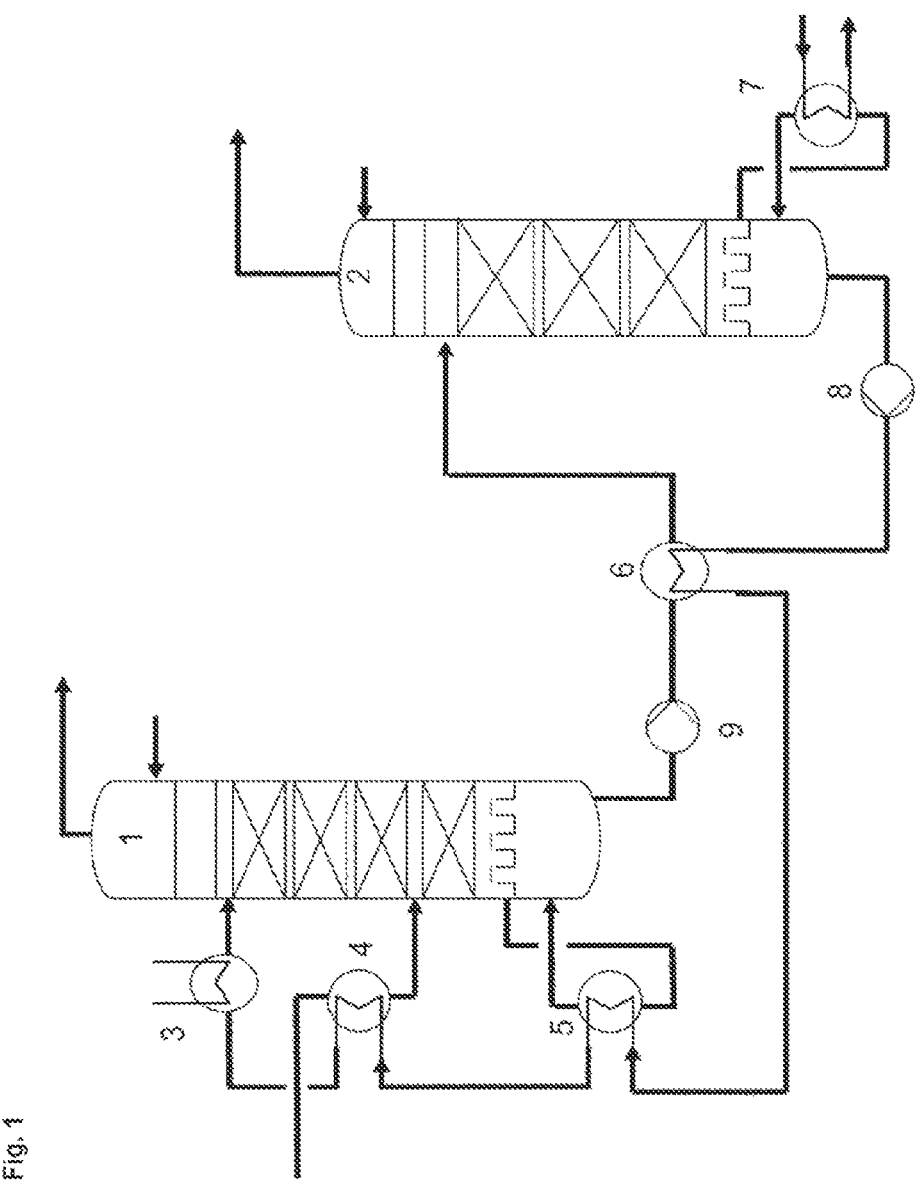
FIG. 1 shows a first embodiment of the present invention.

One advantage of the present process is the relatively simple construction of the heat integration which nevertheless allows efficient energy recovery. The simplest embodiment of the present invention further does not mandate additional side evaporators which entail additional plant engineering complexity and thus higher costs.

The heat integration removes heat from the solvent. The reason for this is not only that other streams or columns are to be heated therewith but rather primarily the cooling of the solvent for the absorption. The absorption of the butenes (here: step a) is usually carried out at a lower temperature than the desorption (here: step b). If in the course of the heat integration sufficient heat is withdrawn from the solvent, i.e. it has a suitable temperature, the solvent may be passed directly into the absorber. However, it is also conceivable that despite the heat integration present the solvent does not yet have the correct temperature. In such a case the solvent may be passed through a residual cooler to be cooled to a suitable temperature after the heat integration and before entry into the absorber.

Heat is a process parameter. The heat supplied or removed corresponds to the change in internal energy minus the work done. The terms heat, heat transport and heat integration used in the present invention are in every instance based on this definition.

The present process relates to the separation of butenes from butene-containing C4-hydrocarbon streams. These streams typically contain not only the butenes but also alkanes (n-butane, isobutane). In the context of the present invention—unless something else is being described—the term butanes is to be understood as meaning both n-butane and isobutane. The process according to the invention may therefore employ any C4-hydrocarbon streams which contain at least butenes and butanes provided that the amounts in which the butenes and/or butanes are present allow economic performance of the process. In a preferred embodiment of the present invention the employed C4-hydrocarbon stream consists essentially, i.e. to an extent of more than 98% by weight, preferably to an extent of more than 99% by weight, of butanes and butenes. The corresponding streams may also contain impurities or other hydrocarbons, such as 1,3-butadiene or C5-hydrocarbons, in small amounts.

In the extraction process according to the invention, a liquid solvent which dissolves primarily the butenes of the employed gaseous C4-hydrocarbon stream is employed. Suitable solvents are aprotic solvents, for example N-methyl-2-pyrrolidone (NMP). The process according to the invention is preferably performed with NMP as the solvent. In a further preferred embodiment of the present invention the solvent contains water, in particular in the range from 1% to 10% by weight, preferably from 4% to 9% by weight, in each case based on the total amount of solvent.

Absorbers that may be employed include in particular random-packed columns which comprise at least two random-packing beds. Such columns are known in principle to those skilled in the art. Preferably arranged above the first random-packing bed is a backwashing zone comprising a plurality of theoretical trays to hold back the solvent entrained in the gas phase. Above the backwashing zone is the top of the absorber where a stream enriched in butenes relative to the employed C4-hydrocarbon stream is obtained. The liquid collector according to the invention would be arranged below the last random-packing bed, the bottom of the absorber being arranged below said collector. The exact construction of the absorber depends on various parameters and is variable in certain aspects.

The liquid solvent is supplied to the absorber spatially above the inlet for the C4-hydrocarbon stream. In a preferred embodiment the solvent is supplied to the absorber above the first random-packing bed and the C4-hydrocarbon stream is added to the absorber in one or more random-packing beds below the first random-packing bed. In the absorber the liquid solvent will trickle downwards and is brought into contact with the (ascending) vaporous C4-hydrocarbon stream to transfer a portion of the C4-hydrocarbon stream containing predominantly butenes to the solvent to form a laden solvent. In step a the C4-hydrocarbon stream and the solvent are brought into contact with one another in particular in countercurrent. In a preferred embodiment of the present invention the portion of the C4-hydrocarbon stream transferred to the solvent comprises at least 70% by weight, particularly preferably at least 80% by weight, of butenes based on the composition of the portion of the C4-hydrocarbon stream transferred to the solvent. This has the result that in particular at least 80%, particularly preferably at least 90%, of the butenes present in the employed C4-hydrocarbon stream are transferred to the solvent.

The laden solvent flows downwards in the absorber and is collected in a suitable liquid collector, in particular a chimney tray. The temperature of the laden solvent obtained in the liquid collector is preferably between 40° C. and 90° C., particularly preferably between 45° C. and 65° C. The laden solvent is withdrawn from the liquid collector, run through an absorber evaporator and then passed into the bottom of the absorber below the liquid collector to outgas predominantly butanes from the laden solvent. The absorber evaporator is preferably a once-through evaporator where the laden solvent is passed through the evaporator only once. This allows achievement of the lowest possible temperatures, thus making it possible to prevent fouling. The driving temperature difference is additionally increased, thus allowing even more efficient energy utilization of the NMP stream. The absorber evaporator may also be configured as a multi-stage apparatus, i.e. a plurality of heat exchangers or a plurality of evaporators belonging to the absorber evaporator may be present.

The solvent laden predominantly with butenes then remains in the bottom and is withdrawn therefrom and passed to the desorber as bottoms stream. The temperature in the bottoms stream of the absorber, which is passed to the desorber, is preferably between 70° C. and 130° C., particularly preferably between 85° C. and 120° C.

In particular, a stream enriched in butanes relative to the employed C4-hydrocarbon stream is then obtained at the top of the absorber. The head pressure in the absorber may be between 3 and 7 bar absolute, preferably between 4 and 6.5 bar absolute. The stream enriched in butanes may additionally contain water originating from the solvent. This water may be separated in a subsequent step. The stream enriched in butanes is withdrawn at the top of the absorber and subjected to a single-or multi-stage condensation to condense out a water-containing stream and a butane-containing product stream. These two streams may be separated from one another in a suitable apparatus, for example a spider. The water-containing stream separated from the butane-containing product stream may be passed to the absorber or to the desorber and/or partially discharged from the process depending on its composition.

The butane-containing product stream thus obtained from the condensation may still contain small amounts of water. In particular in an amount of up to 1500 ppmw, based on the total composition of the butane-containing product stream. In addition, the butane-containing product stream obtained from the condensation may further contain residual butenes, wherein the streams contain typically less than 20% by weight, preferably less than 15% by weight, particularly preferably less than 5% by weight, of butenes based on the total composition of the butane-containing product stream.

Depending on the requirements for the obtained butane-containing product stream it may be necessary for the butane-containing product stream to be subjected to a drying following the condensation, preferably in a drying column, to separate the water still present. The butane-containing product stream preferably contains a maximum amount of water of 50 ppmw, preferably of 25 ppmw, after the drying. The water obtained during the drying may be recycled to the condensation in the absorber.

The solvent withdrawn at the bottom of the absorber and laden predominantly with butenes is supplied to the desorber. To this end the laden solvent may be passed to the desorber using a pump for example. Relative to the bottom of the absorber the bottom of the desorber is at an elevated temperature and preferably a lower pressure. The temperature in the bottom of the desorber is preferably between 120° C. and 200° C., more preferably between 130° C. and 195° C. The head pressure in the desorber may be between 1 and 6 bar absolute, preferably between 2 and 5 bar absolute. The elevated temperature and the preferably lower pressure relative to the absorber has the result that the butenes and optionally any butanes still present are at least partially removed from the solvent. In a preferred embodiment the solvent at least partially freed of butenes contains up to 5000 ppmw of butenes, particularly preferably 100 to 900 ppmw of butenes. The solvent at least partially freed of butenes flows downwards in the desorber and is collected in the liquid collector of the desorber. From there the solvent at least partially freed of butenes is passed through a desorber evaporator and then passed into the bottom of the desorber below the liquid collector, in particular a chimney tray, to outgas any butenes remaining in the solvent. The desorber evaporator is preferably a once-through evaporator where the solvent at least partially freed of butenes is passed through the evaporator only once. This allows achievement of the lowest possible temperatures, thus making it possible to prevent fouling. The desorber evaporator may also be configured as a multi-stage apparatus, i.e. a plurality of heat exchangers belonging to the desorber evaporator may be present. The solvent freed of butenes then remains in the bottom and is withdrawn therefrom, passed to the absorber as bottoms stream and reused there as solvent for the absorption of butenes.

Before being passed to the absorber the solvent freed of butenes may be partially or completely subjected to a regeneration to remove impurities, for example the abovementioned by-products present in the employed C4-hydrocarbon stream and/or formed from the butenes at the temperatures in the desorber such as oligomeric or polymeric compounds, from the solvent, preferably the NMP. The regeneration is preferably performed such that the solvent freed of butenes is passed into a container and evaporated at a pressure of less than 500 mbar absolute, more preferably of less than 200 mbar absolute and a temperature between 100° C. and 150° C. The container may have a column connected to it. Heavy boilers in particular are separated by the regeneration. If only a portion of the solvent freed of butenes is subjected to a regeneration the regenerated portion of the solvent is subsequently combined with the unregenerated solvent and recycled to the absorber.

Especially a stream enriched in butenes relative to the employed C4-hydrocarbon stream is then obtained at the top of the desorber. This stream enriched in butenes may additionally contain water originating from the solvent. This water may be separated in a subsequent step. The stream enriched in butenes is withdrawn at the top of the desorber and subjected to a single-or multi-stage condensation to condense out a water-containing stream which may contain not only water but also residues of organics as well as a butene-containing product stream. These two streams may be separated from one another in a suitable apparatus, for example a spider. The water-containing stream separated from the butene-containing product stream may then be recycled to the desorber. Discharging the entirety or portions of the water-containing stream to remove the organics is also possible.

In a preferred embodiment of the present invention the condensation of the stream enriched in butenes withdrawn at the top of the desorber is configured as a two-stage condensation, wherein in a first stage a water-containing stream is condensed out and then recycled to the desorber and in the second stage the butene-containing product stream is condensed out. However, it may also be the case that water remaining is also condensed out in the second stage. This residual water may be separated from the butene-containing product stream via a suitable apparatus, for example a spider.

The butene-containing product stream obtained from the condensation preferably contains less than 20% by weight, more preferably less than 16% by weight, of butanes based on the total composition of the butene-containing product stream. By contrast, the butene-containing product stream obtained from the condensation preferably has a butene content of at least 70% by weight, more preferably of at least 75% by weight, particularly preferably of at least 86% by weight, based on the total composition of the butene-containing product stream.

A characterizing feature of the present invention is the heat integration using the heat of the solvent on the way from the desorber to the absorber and of the hot condensate which is obtained in the desorber evaporator. The heat of the solvent, preferably of the NMP, withdrawn as a bottoms stream of the desorber is according to the invention used for heat integration by employing the heat of the solvent in at least one respective heat exchanger for preheating the laden solvent passed to the desorber, for evaporation in the absorber evaporator and for evaporation of the liquid C4-hydrocarbon stream.

In a preferred embodiment of the present invention the preheating of the laden solvent passed to the desorber is performed in two stages, wherein a first heat transfer to the laden solvent passed to the desorber is effected in a heat exchanger, preferably a tube bundle heat exchanger, and a second heat transfer to the laden solvent passed to the desorber is effected in a kettle evaporator. Such an embodiment has the advantage that in the abovementioned preferred embodiment the heat transferred to the laden solvent in both stages, i.e. In the heat exchanger and in the kettle evaporator, originates from the solvent withdrawn as the bottoms stream of the desorber as heat transfer medium. The use of a kettle evaporator would also have the advantage that it would allow there to be a lower supply pressure in the conduit to the desorber. A high supply pressure is normally necessary to prevent evaporation in the pipe conduit that could lead to problems including bursting of the pipe conduit. A further advantage is that the thermal load is limited, thus ensuring that the temperature difference is/remains sufficiently large for heat transfer.

According to the invention the solvent, preferably NMP, at least partially freed of butenes is collected in a liquid collector of the desorber and passed through a desorber evaporator to allow outgassing of any butenes remaining in the solvent. The heat for evaporation in the desorber evaporator may be introduced in a heat exchanger by heat transfer from a suitable heat transfer medium. The heat transfer medium may be in particular heating steam employed in the form of medium pressure or high pressure steam. A preferred heating steam is medium pressure steam having a temperature of 150° C. to 270° C., preferably of 160° C. to 250° C.

The medium pressure steam preferably has a pressure of 15 to 30 bar absolute particularly preferably of 17 to 25 bar absolute. Also employable as heating steam is steam having a pressure of >30 bar absolute. Such heating steam may also be referred to as high pressure steam.

The heating steam used for evaporation may undergo at least partial condensation in the heat exchanger, thus generating a hot condensate at a pressure of 10 to 20 bar absolute, preferably 12 to 17 bar absolute, and a temperature of 150° C. to 210° C., preferably 160° C. to 200° C. Preferably arranged downstream of the heat exchanger is a condensate container in which the hot condensate may be separated from the steam. The pressure in the condensate container is preferably lower than in the heat exchanger on the heating steam side. The lower pressure may result in a portion of the hot condensate evaporating, as a result of which the combined steam. i.e. the uncondensed proportion of the heating steam and the hot condensate evaporated in the condensate container by decompression, is obtained as low pressure steam in the condensate container. In the present case the low pressure steam preferably has a pressure of more than 0 bar and less than 10 bar absolute. The temperature of the low pressure steam is preferably 100° C. to 180° C.

The low pressure steam obtained there still contains energy but this is not utilized in any known process. This is not advantageous from an energetic or economic standpoint, however. However, this energy can be utilized in a preferred embodiment of the present invention. To this end, the heating steam used for evaporation in the desorber evaporator may be provided using a, preferably controllable, steam ejector (thermocompressor). The thermocompressor is then supplied both with the employed heating steam, originating from an appropriate steam network for example, here especially the preferably employed medium pressure steam, and also with the low pressure steam from the condensate container, thus forming a mixed steam which is accordingly the heat transfer medium for the desorber evaporator. In this embodiment the mixed steam is accordingly the heating steam. Such a steam ejector is configured such that it is operated with motive steam and by means of negative pressure (back pressure in the steam ejector) can aspirate suction steam from a container to then form the mixed steam employed as the heat transfer medium. The motive steam is in the present case the heating steam/the medium pressure steam, with which the low pressure steam is aspirated from the condensate container as suction steam and mixed with the motive steam.

The advantage of such an embodiment is obvious. The energy of the low pressure steam obtained in the condensate container may be utilized, thus saving energy and costs. Such a procedure can also be advantageous for another reason. The employed steam ejector may be controllable such that the amounts of medium or high pressure and low pressure steam can be adjusted, for example according to particular process parameters. The amount of suction steam is adjusted via the amount of motive steam. The amounts of low pressure and medium pressure steam may be adjusted for example according to the temperature in the desorber.

In a further preferred embodiment the desorber comprises a side evaporator. In such a case the heat transfer medium used for the side evaporator may be the mixed steam from the steam ejector while the desorber evaporator employs medium pressure steam as heating steam. The hot condensate from the desorber evaporator and the side evaporator are then passed to a condensate container according to the above embodiments. The low pressure steam obtained there is then used in the steam ejector, whose mixing steam is employed in the side evaporator. The advantage of this variant is that the hot condensate obtained can be further decompressed to be able to provide a greater amount of low pressure steam.

The presently described process may be employed in integrated chemical systems which comprise in particular an oligomerization and optionally a hydroformylation. It is possible for the separation of butenes by the process according to the invention to be employed at various points in the integrated plant. It is also possible for the separation of butenes according to the invention to be present at various points within an integrated chemical plant. For example the process described here may be employed at the beginning of such an integrated system. The employed C4-hydrocarbon stream may then be in particular a crack C4, a raffinate 1, a raffinate 2 or a mixture thereof. If crack C4 and/or raffinate 2 are employed the separation process according to the invention may have arranged upstream of it a crack C4 hydrogenation in which butadiene is selectively hydrogenated or a butadiene separation in which butadiene is extractively removed with a solvent such as NMP or nitriles to reduce the content of butadiene. It is possible to arrange a hydroisomerization downstream of an extractive butadiene separation and upstream of the separation according to the invention to facilitate the separation task in the process according to the invention since this converts 1-butene into 2-butene which is more readily absorbed by the solvent.

If the separation process is employed at the beginning of the integrated system the obtained product stream may be supplied to an MTBE synthesis which may then preferably be followed successively by a 1-butene separation, an oligomerization and one or more hydroformylations of the purified oligomers. A hydroformylation may be carried out not only with the product stream from the oligomerization, thus making it possible to produce for example INA (isononanol) from di-n-butenes after subsequent hydrogenation or ITDA (isotridecanal) from tributenes, but also with the unconverted butenes of the oligomerization, thus making it possible to produce 2-PH (2-propylheptanol) after subsequent aldol condensation followed by hydrogenation. The unconverted butenes from the oligomerization could optionally also be used to operate a further oligomerization instead of a hydroformylation. The conditions of the individual process steps are familiar to those skilled in the art. The individual process steps may comprise further steps, such as for example the separation of the products or the workup of the resulting stream, but these are not explicitly mentioned here. However, the separation process according to the invention may also be introduced at any other point of such an integrated system.

In one embodiment or the present invention the C4 hydrocarbon stream employed in the separation process according to the invention is withdrawn from an MTBE synthesis after separation of MTBE and the butene-containing product stream is subsequently supplied to a 1-butene separation, after which an oligomerization and one or more hydroformylations for subsequent production of 2-PH, ITDA and/or INA are successively carried out. The individual process steps may comprise further steps, such as for example the separation of the products or the workup of the resulting stream, but these are not explicitly mentioned here.

In a further embodiment of the present invention the C4-hydrocarbon stream employed in the separation process according to the invention is withdrawn from a 1-butene separation and the butene-containing product stream is subsequently supplied to an oligomerization, after which one or more hydroformylations for subsequent production or 2-PH, ITDA and/or INA are carried out. The individual process steps may comprise further steps, such as for example the separation of the products or the workup of the resulting stream, but these are not explicitly mentioned here.

In a further embodiment of the present invention the C4-hydrocarbon stream employed in the separation process according to the invention is withdrawn from an oligomerization and the butene-containing product stream is subsequently supplied to a hydroformylation for subsequent production of 2-PH. The individual process steps may comprise further steps, such as for example the separation of the products or the workup of the resulting stream, but these are not explicitly mentioned here.

In a further embodiment of the present invention the separation process according to the invention is employed at the end of the integrated system. In that case the employed C4-hydrocarbon stream is withdrawn from a 2-PH production downstream of the hydroformylation. The butene-containing product stream then obtained from the separation process according to the invention may in this case be recycled and employed at a suitable point in the integrated system, for example for 1-butene separation, for oligomerization or one or more hydroformylations. This makes it possible to enhance the efficiency of the overall integrated system since even after passing through the last process step in the integrated system up to 20% by weight of butenes may still be present.

Independently of the point in the integrated system where the separation process according to the invention is arranged, the butane-containing product stream may be supplied for example to an adiabatic oligomerization, a hydrogenation of the butenes still present or an n/iso splitting of the butanes where n-butane and isobutane are separated from one another. The n/iso splitting may also be carried out after an adiabatic oligomerization. Another possibility would be inclusion of the butane-containing product stream upstream of the oligomerization in an above-described integrated system composed of MTBE synthesis, 1-butene separation, oligomerization and a hydroformylation.

In a particularly preferred embodiment of the present invention the energy required for n/iso splitting may be effected at least partially by heat integration with the first stage of a two-stage condensation at the top of the desorber. This has the advantage that the energy obtained in the condensation is utilized and not simply released to the environment as in the prior art.

The present invention is hereinbelow elucidated with reference to figures. The figures are for illustration but are not to be understood as limiting.

FIG. 1 shows the basic configuration of the present invention. The liquid C4-hydrocarbon stream is evaporated via a heat exchanger (4) and passed into the absorber (1). The solvent is—where necessary—brought to the desired temperature via a residual cooler (3) and likewise passed into the absorber, wherein the inlet is spatially above the inlet for the C4 hydrocarbon stream, in the present case above the first random-packing bed. Obtained at the top of the absorber (1) is the stream enriched in butanes which is withdrawn. A possible condensation is not shown here—only the recycling of a possible substream is shown. The laden solvent is collected in the bottom of the absorber (1) as indicated by the chimney tray in the figure. There, at least a portion of the laden solvent is withdrawn and passed to the bottom of the absorber (1) via an absorber evaporator (5). The laden solvent is withdrawn from the bottom of the absorber (1) and using a pump (9) passed via the heat exchanger (6) for preheating of the laden solvent to the desorber (2) where the butenes present in the solvent are separated from the solvent. The stream enriched in butenes is obtained at the top of the desorber. This stream can be subjected to a single- or multi-stage condensation which is not shown in the figure. Only a possible recycle stream is indicated. The solvent at least partially freed of butenes is collected in the bottom of the desorber (2) as indicated by the chimney tray in the figure. There, at least a portion of the laden solvent is withdrawn and passed to the bottom of the desorber via a desorber evaporator (7). The solvent freed of butenes is then withdrawn from the bottom of the desorber (2) and using a pump (8) recycled to the absorber via the heat exchanger (6) for preheating the laden solvent, the absorber evaporator (5), the heat exchanger (4) for evaporating the C4-hydrocarbon stream and the residual cooler (3).

Figure 2:
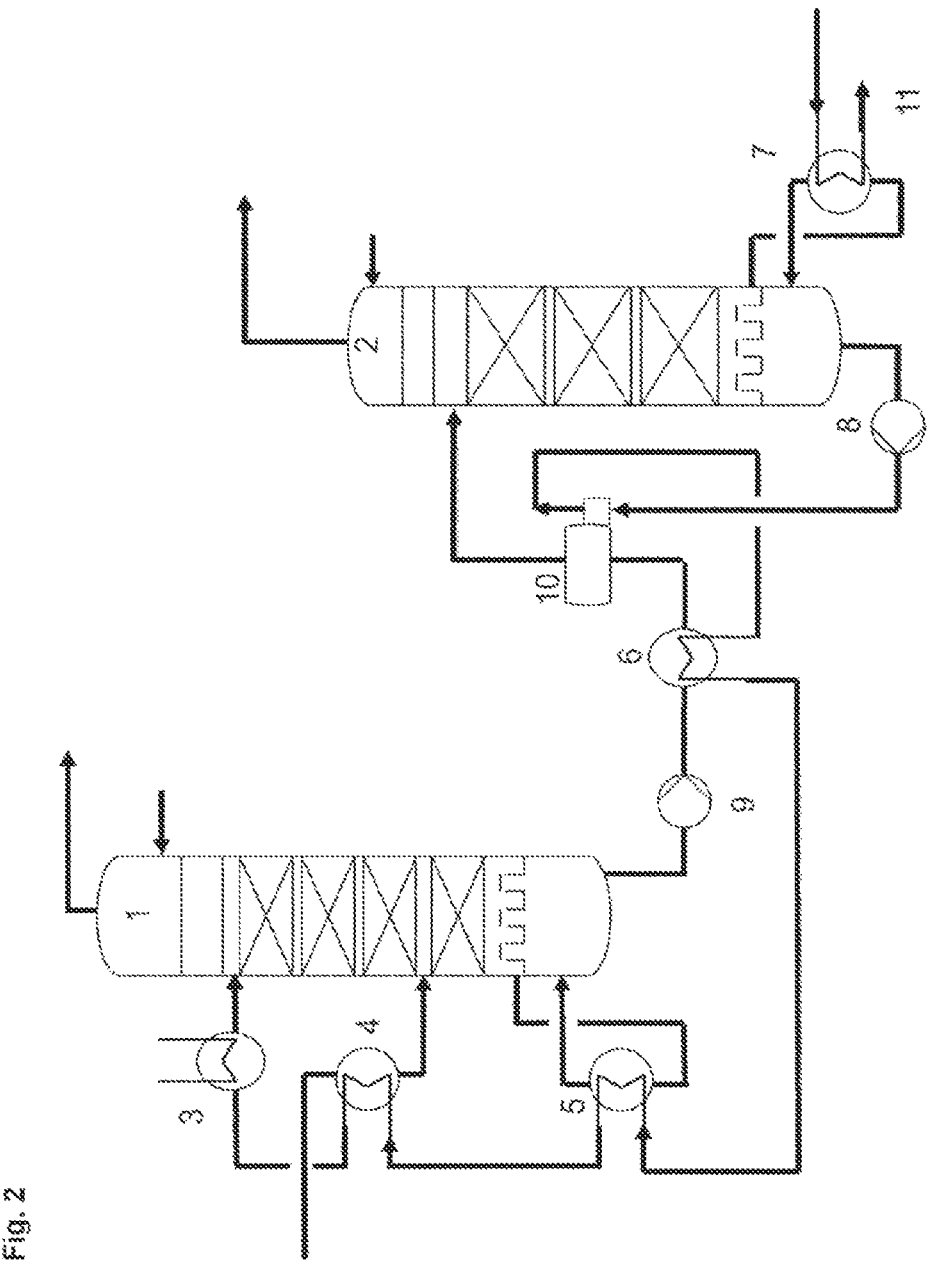
FIG. 2 shows a second embodiment of the present invention.

FIG. 2 shows a preferred embodiment of the present invention where the preheating of the laden solvent passed to the desorber (2) is performed in two stages. The first heat transfer is carried out at the heat exchanger (6) and then the second heat transfer is carried out in the kettle evaporator (10). The mode of operation of a kettle evaporator is elucidated in the description of FIG. 5. Everything else corresponds to what has been previously specified in connection with FIG. 1.

Figure 3:
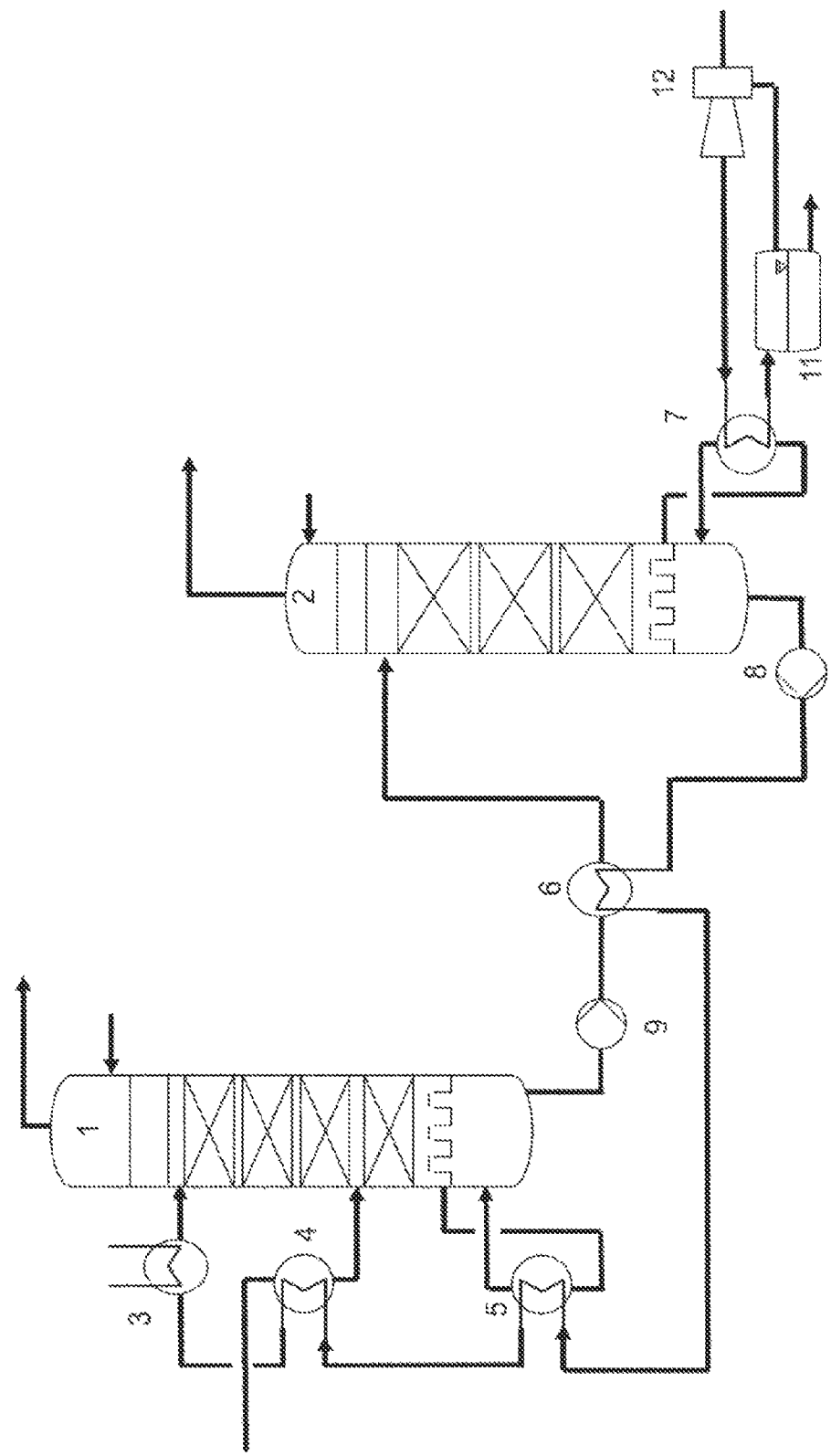
FIG. 3 shows a third embodiment of the present invention.

FIG. 3 shows a further preferred embodiment of the present invention where a steam ejector (12) is present at the desorber evaporator (7). This steam ejector is supplied with the regular heating steam, i.e. for example the medium pressure steam from the steam network and the low pressure steam obtained in the condensate container (11), thus forming a mixed steam which is then used as heating steam for the desorber evaporator (7). The mode of operation of a steam ejector is elucidated in the description of FIG. 6. Everything else corresponds to what has been previously specified in connection with FIG. 1.

Figure 4:
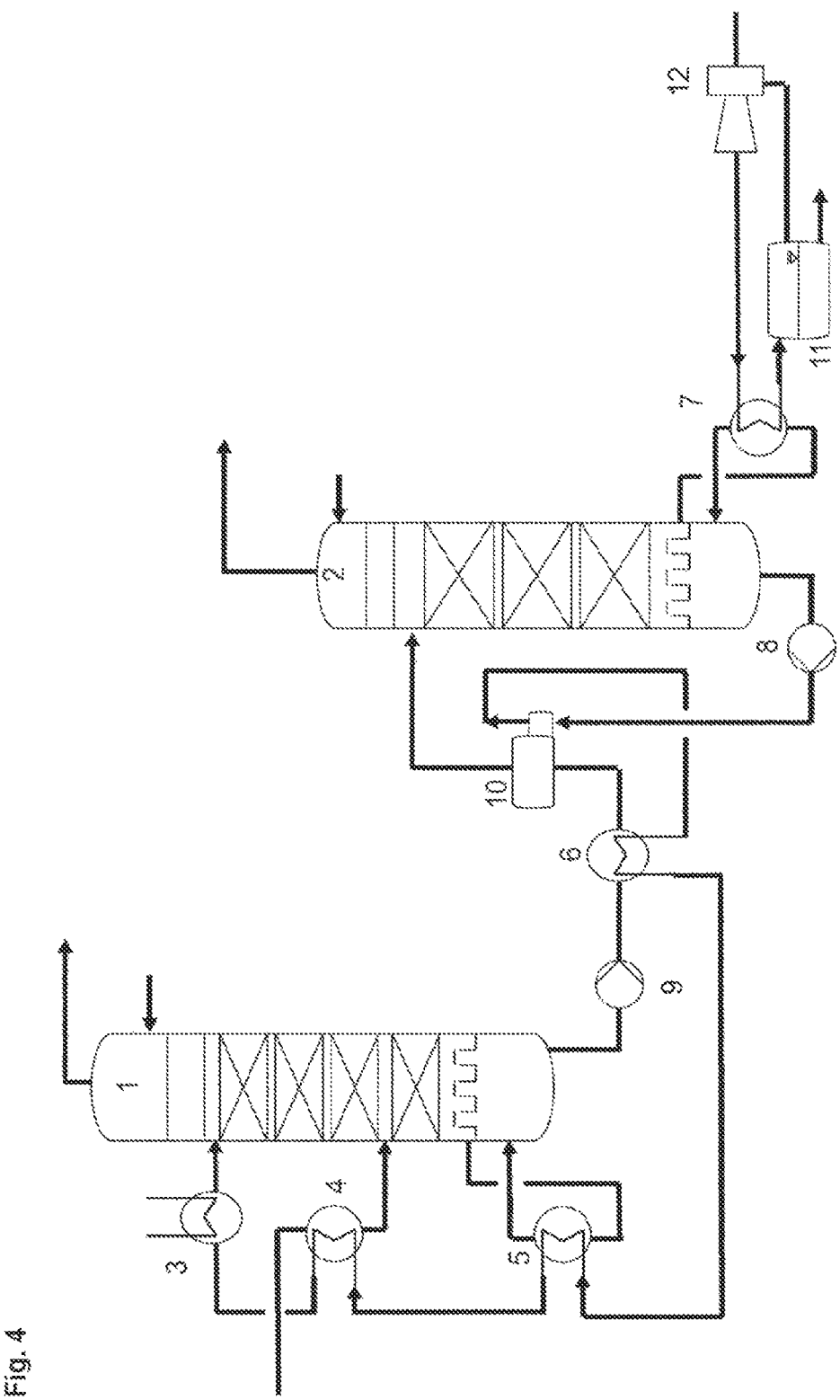
FIG. 4 shows a combination of the two embodiments in FIGS. 2 and 3.

FIG. 4 shows the combination of the two embodiments in FIGS. 2 and 3 where the laden solvent is additionally passed through a kettle evaporator (10) and the desorber evaporator is provided with mixed steam via a steam ejector (12) which is supplied with low pressure steam inter alia from the condensate container (11).

Figure 5:
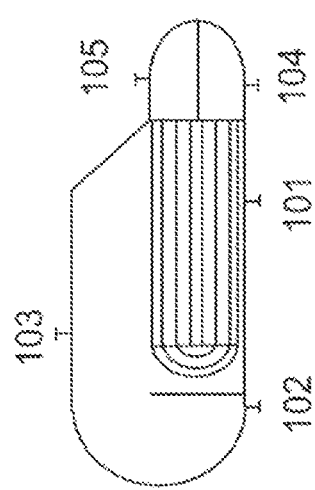
FIG. 5 shows the schematic construction of a kettle evaporator.

FIG. 5 shows the schematic construction of a kettle evaporator (10). The liquid feed is passed into the evaporator via the feed port (101) on the shell side. The liquid feed is partially evaporated in the kettle evaporator and passed into the desorber via the gas port (103) on the shell side. The proportion of the feed that is not evaporated passes over a weir and into the desorber (2) as liquid product via the product port (102) on the shell side. On the tube side the hot bottoms product of the desorber (2) is used as heating medium which is passed through the tubes via the entry port (104) and exits again at the exit port (105).

Figure 6:
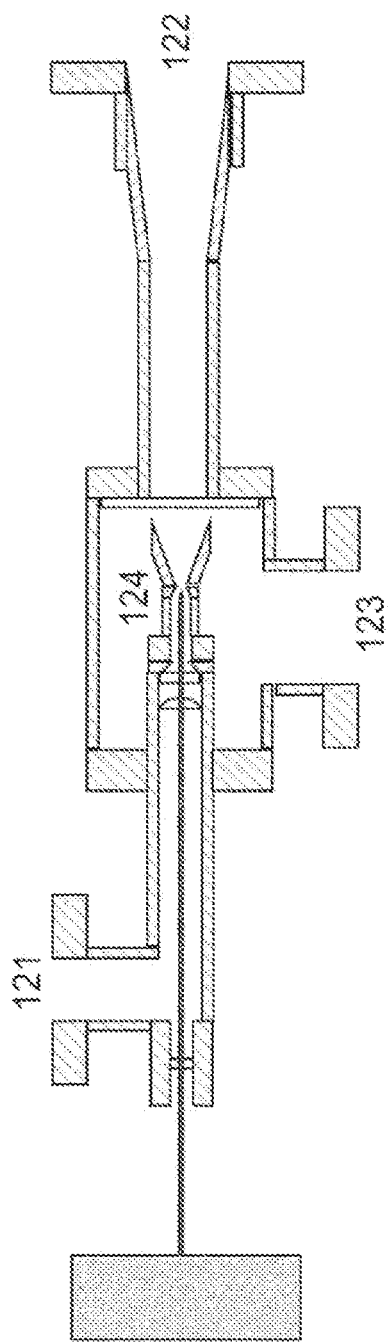
FIG. 6 shows the schematic construction of a steam ejector.

FIG. 6 shows the schematic construction of a steam ejector (12). Here, the motive steam (121) is the heating steam, in particular the medium pressure steam from the steam network. The suction steam (123) is the low pressure steam from the condensate container. The two are mixed via the control unit (124) and via the exit passed to the desorber evaporator (7) as mixed steam (122). The amount of motive steam and suction steam can be adjusted via the control unit, thus making it possible to influence the pressure and temperature of the mixed steam and thus the possible heating output.

EXAMPLES

Example 1—Embodiment According to FIG. 1

The butane-butene separation shown in FIG. 1 was simulated with Aspen Plus v10. A modified NRTL parameter set was used to describe the interactions between the components. In the simulation, 19 t/h of a hydrocarbon-containing feed was run into a butane/butene separation (according to FIG. 1). This contains altogether 45% by weight of butanes, 30% by weight of isobutene and 25% by weight of n-butenes.

Altogether 7 t/h of butane-containing tops product are withdrawn at the absorber. The butane-containing tops product from the absorber consists of 70% by weight n-butane, 27% by weight isobutane and 3% by weight butenes. The solvent laden with the butene-containing product stream is withdrawn in the bottoms. The butene-containing product stream contains 14% by weight n-butane, 47% by weight isobutene and 39% by weight n-butenes. The established solvent/feed ratio of 13 thus makes it possible to achieve a 98% butene yield. The large excess of solvent is then also used for heat integration.

Only at the desorber (2) is energy from outside the plant introduced, namely via the heating steam for the desorber evaporator (7). 6.9 MW are transferred to the desorber evaporator (7). Otherwise a heat integration with the solvent is performed throughout in this example and so no further external energy is required. The hot bottoms product from the desorber (2) is passed to the preheating (6) of the desorber via the heat exchanger. 8.4 MW are transferred here. After the preheating of the desorber (6) the solvent is passed to the bottom of the absorber (1) where 7.8 MW are transferred via the heat exchanger (5) present therein. For evaporation of the C4 feed stream a further 1.8 MW are transferred from the solvent to the feed via the heat exchanger (4) for feed evaporation. In a residual cooler (3) the solvent is brought to the optimal extraction temperature with cooling water. For this example a temperature of 40° C. was assumed. A further 2.5 MW must therefore be withdrawn from the solvent to reach this temperature. This setup allows the external heat input to be reduced and the internal heat to be optimally utilized. If for example at least one of the heat exchangers (4), (5) and (6) were not present the untransferred energy would need to be withdrawn in the residual cooler (3) and thus destroyed. In addition the then untransferred energy would need to be supplied from external sources. This process mode altogether requires only 6.9 MW of external energy (see table 1).

Example 2—Embodiment According to FIG. 2/Kettle Evaporator

The calculations and simulations were performed as in example 1, wherein a kettle evaporator (10) was additionally present. To transfer the heat energy in the heat exchanger (6) of 12 MW the laden solvent must be in liquid form. To this end the sump pump (9) of the absorber (1) must develop a corresponding power. However if the preheater is a multistage preheater, wherein the second stage is a kettle evaporator (10), the pump (9) need only produce a low pressure, thus economizing on pump power. In the case that the thermal energy amount of 8.4 MW is equally divided over both stages, i.e. the heat exchanger (6) and the kettle evaporator (10) each transfer 4.2 MW, the pump can develop 33% less power. This process mode altogether requires only 5.6 MW of external energy (see table 1).

Example 3—Embodiment According to FIG. 3/Steam Ejector

The calculations and simulations were performed as in example 1, wherein a steam ejector (12) was additionally present. Only at the desorber is external energy introduced via the heating steam. According to example 1 this is altogether 6.9 MW. If a steam ejector is employed it is possible to make a saving of about 10%, i.e. 0.69 MW, which are then supplied via the residual heat utilization of the steam ejector. This process mode altogether requires only 4.8 MW of external energy (see table 1).

TABLE 1

Composition of various examples. Example 1 more particularly elucidated in the accompanying text.

|  | Example 1 | Example 2 | Example 3 |
|---|---|---|---|
| Feed [t/h] | 19 | 16 | 13 |
| Butane proportion in the feed [% by wt.] | 45 | 39 | 23 |
| Butane stream [t/h] | 7 | 5 | 3 |
| Butane proportion in the butane stream [% by wt.] | 97 | 96 | 92 |
| Butene yield [%] | 98 | 98 | 98 |
| Solvent/feed ratio [—] | 13 | 13 | 13 |
| External energy amount [MW] | 6.9 | 5.6 | 4.8 |

The invention claimed is:

1. A process for separating butenes from a C4-hydrocarbon stream which contains at least butenes and butanes by extractive distillation with a solvent, the process comprising:
   a. at least partially evaporating a liquid C4-hydrocarbon stream in a feed evaporator, to supply a gaseous C4-hydrocarbon stream and supplying the solvent above the gaseous C4-hydrocarbon stream to an absorber in which the gaseous C4-hydrocarbon stream and the solvent are contacted with one another to transfer predominantly butenes from the gaseous C4-hydrocarbon stream to the solvent, to obtain a laden solvent, wherein the laden solvent is collected in a liquid collector of the absorber and passed through an absorber evaporator and then passed into the bottom of the absorber below the liquid collector to outgas predominantly butanes from the laden solvent, and wherein the laden solvent is subsequently passed to a desorber as a bottoms stream;
   b. supplying the laden solvent to the desorber, the bottom of which is at an elevated temperature relative to the bottom of the absorber, and in which the butenes are separated from the laden solvent to obtain at the top of the desorber a stream enriched in butenes, wherein the solvent, at least partially freed of butenes, is collected in a liquid collector of the desorber and passed through a desorber evaporator and then passed into the bottom of the desorber below the liquid collector to outgas any butenes remaining in the solvent and wherein the solvent is subsequently recycled to the absorber as a bottoms stream;
   wherein heat of the solvent withdrawn as the bottoms stream of the desorber is used at least partially for heat integration by employing the heat of the solvent in at least one respective heat exchanger for preheating the laden solvent passed to the desorber, for evaporation in the absorber evaporator, and for evaporation of the liquid C4-hydrocarbon stream,
wherein an employed heating steam undergoes at least partial condensation in the at least one respective heat exchanger, thus generating a hot condensate at a pressure of 10 to 20 bar absolute, and a temperature of 150° C. to 210° C., which is passed to a condensate container.

2. The process according to claim 1, wherein the solvent is N-methyl-2-pyrrolidone (NMP).

3. The process according to claim 1, wherein the solvent contains water and a water content is between 1% and 10% by weight.

4. The process according to claim 1, wherein a stream enriched in butanes relative to the C4-hydrocarbon stream is obtained at the top of the absorber.

5. The process according to claim 1, wherein the stream enriched in butenes obtained at the top of the desorber additionally contains water originating from the solvent.

6. The process according to claim 5, wherein the stream enriched in butenes is withdrawn at the top of the desorber and subjected to a condensation, wherein a water-containing stream and a butene-containing product stream are condensed out and separated from one another.

7. The process according to claim 6, wherein the butene-containing product stream obtained from the condensation has a butene content of at least 70% by weight, based on a total composition of the butene-containing product stream.

8. The process according to claim 1, wherein a temperature in the bottoms stream of the absorber, which is passed to the desorber, is between 70° C. to 130°C.

9. The process according to claim 1, wherein a temperature in the bottom of the desorber is between 120° C. and 200° C.

10. The process according to claim 1, wherein a head pressure in the desorber is between 1 and 6 bar absolute.

11. The process according to claim 1, wherein the preheating of the laden solvent passed to the desorber is performed in two stages, wherein a first heat transfer to the solvent is effected in a heat exchanger and a second heat transfer to the solvent is effected in a kettle evaporator.

12. The process according to claim 1, wherein the heat for evaporation in the desorber evaporator is introduced in a heat exchanger by heat transfer with a suitable heat transfer medium.

13. The process according to claim 1, wherein a pressure in the condensate container is lower than in a heating steam side of the heat exchanger, thus causing a portion of the heating condensate to be re-evaporated, as a result of which the combined steam is obtained as low pressure steam.

14. The process according to claim 13, wherein the heating steam for the desorber evaporator is provided using a steam ejector supplied with high pressure or medium pressure steam and the low pressure steam obtained in the condensate container.

15. The process according to claim 1, wherein the bottom of the desorber is at a lower pressure relative to the bottom of the absorber.

16. The process according to claim 1, wherein the hot condensate is generated at a pressure of 12 to 17 bar absolute.

17. The process according to claim 1, wherein the hot condensate is generated at a temperature of 160° C. to 200° C.

18. The process according to claim 3, wherein the water content is between 4% and 9% by weight.

19. The process according to claim 7, wherein the butene-containing product stream has a butene content of at least 86% by weight, based on the total composition of the butene-containing product stream.

* * * * *